(12) United States Patent
Bercovier et al.

(10) Patent No.: US 7,892,557 B2
(45) Date of Patent: *Feb. 22, 2011

(54) PEPTIDE MIMOTOPES OF MYCOBACTERIAL MANNOSYLATED LIPOGLYCANS AND USES THEREOF

(75) Inventors: Herve Bercovier, Jerusalem (IL); Ayelet Barenholz, Jerusalem (IL); Jonathan Gershoni, Herzliya (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 703 days.

This patent is subject to a terminal disclaimer.

(21) Appl. No.: 10/589,866

(22) PCT Filed: Feb. 17, 2005

(86) PCT No.: PCT/IL2005/000199

§ 371 (c)(1),
(2), (4) Date: Sep. 19, 2006

(87) PCT Pub. No.: WO2005/080414

PCT Pub. Date: Sep. 1, 2005

(65) Prior Publication Data

US 2007/0292447 A1     Dec. 20, 2007

Related U.S. Application Data

(60) Provisional application No. 60/545,510, filed on Feb. 19, 2004, provisional application No. 60/582,221, filed on Jun. 24, 2004.

(51) Int. Cl.
*A61K 39/38* (2006.01)
*A61K 39/00* (2006.01)
*A61K 39/04* (2006.01)
*A61K 38/00* (2006.01)

(52) U.S. Cl. .............. 424/185.1; 424/193.1; 424/184.1; 424/248.1; 514/2; 530/300; 530/806; 530/807

(58) Field of Classification Search ........................ None
See application file for complete search history.

(56) References Cited

U.S. PATENT DOCUMENTS 6,699,703 B1 * 3/2004 Doucette-Stamm et al. ...... 435/252.3
7,273,721 B2 * 9/2007 Pompejus et al. .............. 435/41

FOREIGN PATENT DOCUMENTS

WO       93/18150 A1    9/1993
WO    WO 93/18150    *  9/1993
WO       03/049752 A2   6/2003

OTHER PUBLICATIONS

Harlow et al. In: Antibodies: A Laboratory Manual. Cold Spring Harbor Laboratory, Chapter 5, p. 76, 1988.*
Barenholz et al. J. Med. Microbiol. 56: 579-586, 2007.*
Nigou, et al., "Mannosylated Lipoarabinomannans Inhibit IL-12 Production by Human Dendritic Cells: Evidence for a Negative Signal Delivered Through the Mannose Receptor", The Journal of Immunology, vol. 166, pp. 7477-7485, (2001).
Nigou, et al., "Mycobacterial lipoarabinomannans: modulators of dendritic cell function and the apoptotic response", Microbes and Infection, vol. 4, pp. 945-953, (2002).
Olson, et al., "Design and Synthesis of a Protein β-Turn Mimetic", J. Am. Chem. Soc., vol. 112, pp. 323-333, (1990).
Pincus, et al., "Peptides That Mimic the Group B Streptococcal Type III Capsular Polysaccharide Antigen", the Journal of Immunology, vol. 160, pp. 293-298, (1998).
Prinzis, et al., "Structure and anitgenicity of lipoarabinomannan from *Mycobacterium bovis* BCG", Journal of General Microbiology, vol. 139, pp. 2649-2658, (1993).
Quesniaux, et al., "Toll-Like Receptor 2 (TLR2)-Dependent-Positive and TLR2-Independent-Negative Regulation of Proinflammatory Cytokines by Mycobacterial Lipomannans", The Journal of Immunology, vol. 172, pp. 4425-4434, (2004).
Schlesinger, et al., "Binding of the Terminal Mannosyl Units of Lipoarabinomannan from a Virulent Strain of Mycobacterium Tuberculosis to Human Macrophages", Journal of Immunology, vol. 152, pp. 4070-4079, (1994).
Sethi, et al., "Contraction-Mediated Pinocytosis of RGD-Peptide by Dermal Fibroblasts: Inhibition of Matrix Attachment Blocks Contraction and Disrupts Microfilament Organisation", Cell Motility and Cytoskeleton, vol. 52, pp. 231-241, (2002).
Shirakawa, et al., "The Inverse Association Between Tuberculin Responses and Atopic Disorder", Science, vol. 275, pp. 77-79, (1997).

(Continued)

*Primary Examiner*—S. Devi
(74) *Attorney, Agent, or Firm*—The Nath Law Group; Susanne M. Hopkins; Ari G. Zytcer

(57) ABSTRACT

The present invention relates to the identification of antigenic and immunogenic peptide-based mimicry of mannose-containing cell-wall compounds characterizing mycobacterial infectious agents, such as *Mycobacterium tuberculosis.*

Amino acid molecules which are mimotopes of mannosylated lipoglycans, such as lipoarabinomannan (ManLAM), including at least one of the following characteristics: (a) being capable of binding to ManLAM binding antibodies; (b) being capable of eliciting production of ManLAM binding antibodies, are provided.

Also diagnostic methods for diagnosing mycobacterial infections and methods of vaccinating subjects against such infections. The diagnostic and vaccination methods employ the provided amino acid molecules.

Accordingly, a diagnostic kit and a vaccine for executing the aforementioned methods are provided.

14 Claims, 5 Drawing Sheets

OTHER PUBLICATIONS

Shirtcliffe, et al., "An inverse correlation between estimated tuberculosis notification rates and asthma symptoms", Respirology, vol. 7, pp. 153-155, (2002).

Singh, et al., "Advances in Vaccine Adjuvants for Infectious Diseases", Current HIV Research, vol. 1, pp. 309-320, (2003).

Smith, et al., "Libraries of Peptides and Proteins Displayed on Filamentous Phage", Methods in Enzymology, vol. 217, pp. 228-257, (1993).

Stern, et al., "Helical epitopes determined by low-stringency antibody screening of a combinatorial peptide library", FASEB J., vol. 11, pp. 147-153, (1997).

Temkin, et al., "Tumor necrosis factors in a murine model of allergic peritonitis: effects on eosinophil accumulation and inflammatory mediators' release", Cytokine, vol. 24, pp. 74-80, (2003).

Tibbetts, et al., "Linear and cyclic LFA-1 and ICAM-1 peptides inhibit T cell adhesion and function", Peptides, vol. 21, pp.1161-1167, (2000).

Valadon, et al., "Enhancement of ELISAs for screening peptides in epitope phage display libraries", Journal of Immunological Methods, vol. 197, pp. 171-179, (1996).

Von Mutius, et al., "International patterns of tuberculosis and the prevalence of symptoms of asthma, rhinitis, and eczema", Thorax, vol. 55, pp. 449-453, (2000).

Vyas, et al., "Structural basis of peptide-carbohydrate mimicry in an antibody-combining site", PNAS, vol. 100, No. 25, pp. 15023-15028, (2003).

Wang, et al., "Epitope Identification and Discovery Using Phage Display Libraries: Applications in Vaccine Development and Diagnostics", Current Drug Targets, vol. 5, pp. 1-15, (2004).

Wu, et al., "The Pharmacological Actions of Nicotine on the Gastrointestinal Tract", Journal of Pharmacological Sciences, vol. 94, pp. 348-358, (2004).

Yoshimura, et al., "Role of NFκB in antigen presentation and development of regulatory T cells elucidated by treatment of dendritic cells with the proteasome inhibitor PSI", Eur. J. Immunol., vol. 31, pp. 1883-1893, (2001).

Zabrocki, et al., "Conformational Mimicry. 1. 1,5-Disubstituted Tetrazole Ring as a Surrogate for the Cis AmideBond", J. Am. Chem. Soc., vol. 110, pp. 5875-5880, (1988).

Zechel, et al., "Synthetic glucagon antagonists and partial agonists", Int. J. Peptide Protein Res., vol. 38, pp. 131-138, (1991).

Zuany-Amorim, et al., "Suppression of airway eosinophilia by killed mycobacerium vaccae-induced allergen-specific regulatory T-cells", Nature Medicine, vol. 8, No. 6, pp.625-629, (2002).

Miyakk, et al., "1,2,3,4-Tetrahydroisoquinoline-3-carboxylic Acid Angiotensin: Synthesis and Angiotensin Converting Enzyme Inhibitory Activity of 1,2,3,4-Tetrahydroisoquinoline-3-carboxylic Acid Derivatives", J. Takeda Res. Labs., vol. 43, pp. 53-76, (1984).

Deluca, et al., "Parenteral Drug-Delivery Systems", Pharmaceutics and Pharmacy Practice, ch. 8, pp. 238-250, J.B. Lippincott Co., Philadelphia, PA., Banker and Chalmers, eds., (1982).

Trissel, "Intravenous Infusion Solutions", ASHP Handbook on Injectable Drugs, 4th ed., pp. 622-630, (1986).

Enshell-Seijffers, et al., "Phage Display Selection and Analysis of Ab-Binding Epitopes", Current Protocols in Immunology, vol. 2, pp. 9.8.1-9.8.27, (2002).

Abad, et al., "Therapeutic Effects of Vasoactive Intestinal Peptide in the Trinitrobenzene Sulfonic Acid Mice Model of Crohn's Disease", Gastroenterology, vol. 124, pp. 961-971, (2003).

Antunes, et al., "Serological screening for tuberculosis in the community: an evaluation of the Mycodot procedure in an African population with high HIV-2 prevalence (Republic of Guinea-Bissau)", Research in Microbiology, vol. 153, pp. 301-305, (2002).

Agrawal, et al., "Novel immunomodulatory oligonucleotides prevent development of allergic airway inflammation and airway hyperresponsiveness in asthma", International Immunopharmacology, vol. 4, pp.127-138, (2004).

Arnold, et al., "Chimeric Rhinoviruses as Tools for Vaccine Development and Characterization of Protein Epitopes", Intervirology, vol. 39, pp. 72-78, (1996).

Barenholz, et al., "A peptide mimetic of the mycobacterial mannosylated lipoarabinomannan: characterization and potential applications", Journal of Medical Microbiology, vol. 56, pp. 579-586, (2007).

Barnes, et al., "Cytokine Production Induced by Mycobacterium tuberculosis Lipoarabinomannan", The Journal of Immunology, vol. 149, No. 2, pp. 541-547, (1992).

Benhar, "Biotechnological applications of phage and cell display", Biotechnology Advances, vol. 19, pp. 1-33, (2001).

Blyth, et al., "Lung inflammation and epithelial changes in a murine model of atopic asthma", Am. J. Respir. Cell Mol. Biol., vol. 14, pp. 425-438, (1996).

Chatterjee, et al. "Lipoarabinomannan of Mycobacterium tuberculosis: Capping with Mannosyl Residues in Some Strains", The Journal of Biological Chemistry, vol. 267, No. 9, pp. 6234-6239, (1992).

Ciesielski, "BCG Vaccination and the PPD test: what the clinician needs to know", J Fam Pract, vol. 40, pp. 76-80, Abstract, (1995).

Dao, et al., "Mycobacterium tuberculosis Lipomannan Induces Apoptosis and Interleukin-12 Production in Macrophages", Infection and Immunity, vol. 72, No. 4, pp. 2067-2074, (2004).

D'Argenio, et al., "Expression of apoptosis-related proteins in rat with induced colitis", Int J Colorectal Dis, vol. 19, pp. 451-490, (2004).

Dimaio, et al., "Synthesis of Chiral Piperazin-2-ones as Model Peptidomimetics", J. Chem. Soc. Perkin Trans. I, pp. 1687-1689, (1989).

Enshell-Seijffers, et al., "The Mapping and Reconstitution of a Conformational Discontinuous B-cell Epitope of HIV-1", J. Mol. Biol., vol. 334, pp. 87-101, (2003).

Garvey, et al., "3,4-Disubstituted γ-Lactam Rings as Conformationally Constrained Mimics of Peptide Derivatives Containing Aspartic Acid or Norleucine", J. Org. Chem., vol. 55, pp. 936-940, (1990).

Glatman-Freedman, "Advances in antibody-mediated immunity against *Mycobacterium tuberculosis*: implications for a novel vaccine strategy", FEMS Immunology and Medical Microbiology, vol. 39, pp. 9-16, (2003).

Greenspan, et al., "Defining epitopes: It's not as easy as it seems", Nature Biotechnology, vol. 17, pp. 836-837, (1999).

Grimaldi, et al., "Depletion of eosinophils in mice through the use of antibodies specific for C-C chemokine receptor 3 (CCR3)", Journal of Leukocyte Biology, vol. 65, pp. 846-853, (1999).

Guérardel, et al., "Structural Study of Lipomannan and Lipoarabinomannan from *Mycobacterium chelonae*", The Journal of Biological Chemistry, vol. 277, No. 34, pp. 30635-30648, (2002).

Hamasur, et al., "*Mycobacterium tuberculosis* arabinomannan-protein conjugates protect against tuberculosis", Vaccine, vol. 21, pp. 4081-4093, (2003).

Hamasur, et al., "Synthesis and immunologic characterisation of *Mycobacterium tuberculosis* lipoarabinomannan specific oligosaccharide-protein conjugates", Vaccine, vol. 17, pp. 2853-2861, (1999).

Hamasur, et al., "Rapid diagnosis of tuberculosis by detection of mycobacterial lipoarabinomannan in urine", Journal of Microbiological Methods, vol. 45, pp. 41-52, (2001).

Harlow, et al., "Antibodies—a laboratory manual", ch. 5, p. 76, (1988).

Hetland, et al., "Involvement of Antilipoarabinomannan Antibodies in Classical Complement Activation in Tuberculosis", Clinical and Diagnostic Laboratory Immunology, vol. 5, No. 2, pp. 211-218, (1998).

Hubeau, et al., "Extended freeze-dried *Mycobacterium bovis* Bacillus Calmette-Guérin induces the release of interleukin-12 but not tumour necrosis factor-α by alveolar macrophages, both in vitro and in vivo", Clin Exp Allergy, vol. 33, pp.386-393, (2003).

Jacobson, et al., "The pneumococcal conjugate vaccine", Minerva Pediatr., vol. 54, pp. 295-303, Abstract, (2002).

Jining, et al., "Design, structure and biological activity of β-turn peptides of CD2 protein for inhibition of T-cell adhesion", Eur. J. Biochem., vol. 271, pp. 2873-2886, (2004).

Jones, et al., "Amide Bond Isosteres: Imidazolines in Pseudopeptide Chemistry", Tetrahedron Letters, vol. 29, No. 31, pp. 3853-3856, (1988).

Kahn, et al., "The Incorporation of β-Turn Prosthetic Units into Merrifield Solid Phase Peptide Synthesis", Tetrahedron Letters, vol. 30, No. 18, pp. 2317-2320, (1989).

Kaur, et al., "Characterization of the epitope of anti-lipoarabinomannan antibodies as the terminal hexaarabinofuranosyl motif of mycobacterial arabinans", Microbiology, vol. 148, pp. 3049-3057, (2002).

Kazmierski, et al., "Topographic Design of Peptide Neurotransmitters and Hormones on Stable Backbone Templates: Relation of Conformation and Dynamics to Bioactivity", J. Am. Chem. Soc., vol. 113, pp. 2275-2283, (1991).

Kazmierski, et al., "Asymmetric Synthesis of Topographically Constrained Amino Acids: Synthesis of the Optically Pure Isomers of a, β-Dimethyl-Phenylalamine and a,β-Dimethyl-1,2,3,4-Tetrahydroisoquinoline-3-Carboxylic Acid", Tetrahedron Letters, vol. 32, No. 41, pp. 5769-5772, (1991).

Kemp, et al., "Conformationally Restricted Cyclic Nonapeptides Derived from L-Cysteine and LL-3-Amino-2-piperidone-6-carboxylic Acid (LL-Acp), a Potent β-Turn-Inducing Dipeptide Analogue", J. Org. Chem., vol. 50, pp. 5834-5838, (1985).

Kemp, et al., "(2S,5S,8S,11S)-1-Acetyl-1,4-Diaza-3-Keto-5-Carboxy-10-Thia-Tricyclo-[2.8.04,8]-Tridecane, 1 the Preferred Conformation of 1 (1 =- α Temp-OH) and its Peptide Conjugates αTemp-L-(Ala)n-OR (n=1 to 4) and a-temp-L-Ala-L-Phe-L-LYS(ε-Boc)-L-Lys(ε-Boc)-NHMe Studies of Templates for α-Helix Formation", Tetrahedron Letters, vol. 29, No. 39, pp. 4935-4938, (1988).

Kemp, et al., "A Convenient Preparation of Derivatives of 3(S)-Amino-10(R)-Carboxy-1,6-Diaza-Cyclodeca-2,7-Dione the Dilactam of L-α,γ-Diaminobutyric Acid and D-Glutamic Acid: a β-Turn Template", Tetrahedron Letters, vol. 29, No. 40, pp. 5057-5060, (1988).

Kemp, et al., "Conformational Analysis of Peptide-Functionalized Diacylaminoepindolidiones 1H NMR Evidence for βSheet Formation", Tetrahedron Letters, vol. 29, No. 40, pp. 5081-5082, (1988).

Kemp, et al., "Amino Acid Derivatives That Stabilize Secondary Structures of Polypeptides. 4. Practical Synthesis of 4(Alkylamino)-3-cyano-6-azabicyclo[3.2.1]oct-3-enes (Ben Derivatives) as y-Turn Templates", J. Org. Chem., vol. 54, pp. 109-115, (1989).

Kibbelaar, et al., "Expression of the Embryonal Neural Cell Adhesion Molecule N-Cam in Lung Carcinoma. Diagnostic Usefulness of Monoclonal Antibody 735 for the Distinction Between Small Cell Lung Cancer and Non-Small Cell Lung Cancer", Journal of Pathology, vol. 159, pp. 23-28, (1989).

Leech, et al., "Regulation of p53 by Macrophage Migration Inhibitory Factor in Inflammatory Arthritis", Arthritis & Rheumatism, vol. 48, No. 7, pp. 1881-1889, (2003).

Locke, et al., "Comparison of Airway Remodeling in Acute, Subacute, and Chronic Models of Allergic Airways Disease", Am J Respir Cell Mol Biol, vol. 36, pp. 625-632, (2007).

Luo, et al., "A Molecular Basis for Functional Peptide Mimicry of a Carbohydrate Antigen", The Journal of Biological Chemistry, vol. 275, No. 21, pp. 16146-16154, (2000).

Maeda, et al., "The Cell Surface Receptor DC-SIGN Discriminates between Mycobacterium Species through Selective Recognition of the Mannose Caps on Lipoarabinomannan", The Journal of Biological Chemistry, vol. 278, No. 8, pp. 5513-5516, (2003).

Maekura, et al., "Clinical Evaluation of Anti-Tuberculous Glycolipid Immunoglobulin G Antibody Assay for Rapid Serodiagnosis of Pulmonary Tuberculosis", Journal of Clinical Microbiology, vol. 39, No. 10, pp. 3603-3608, (2001).

Martin, et al., "T cell cytokines: animal models", Paediatric respiratory reviews, vol. 5, suppl A, pp. S47-S51, (2004).

Meloen, et al., "Review: Mimotopes: realization of an unlikely concept", Journal of Molecular Recognition, vol. 13, pp. 352-359, (2000).

Mukherjee, et al., "Protective Murine Monoclonal Antibodies to *Cryptococcus neoformans*", Infection and Immunity, vol. 60, No. 11, pp. 4534-4541, (1992).

Nagai, et al., "Synthesis of a Bicyclic Dipeptide with the Shape of β-Turn Central Part", Tetrahedron Letters, vol. 26, No. 5, pp. 647-650, (1985).

Navoa, et al., "Specificity and Diversity of Antibodies to *Mycobacterium tuberculosis* Arabinomannan", Clinical and Diagnostic Laboratory Immunology, vol. 10, No. 1, pp. 88-94, (2003).

Neurath, et al., "Antibodies to Interleukin 12 Abrogate Established Experimental Colitis in Mice", The Journal of Experimental Medicine, vol. 182, pp. 1281-1290, (1995).

Nguyen, et al., "Involvement of macrophage mannose receptor in the binding and transmission of HIV by macrophages", Eur. J. Immunol., vol. 33, pp. 483-493, (2003).

* cited by examiner

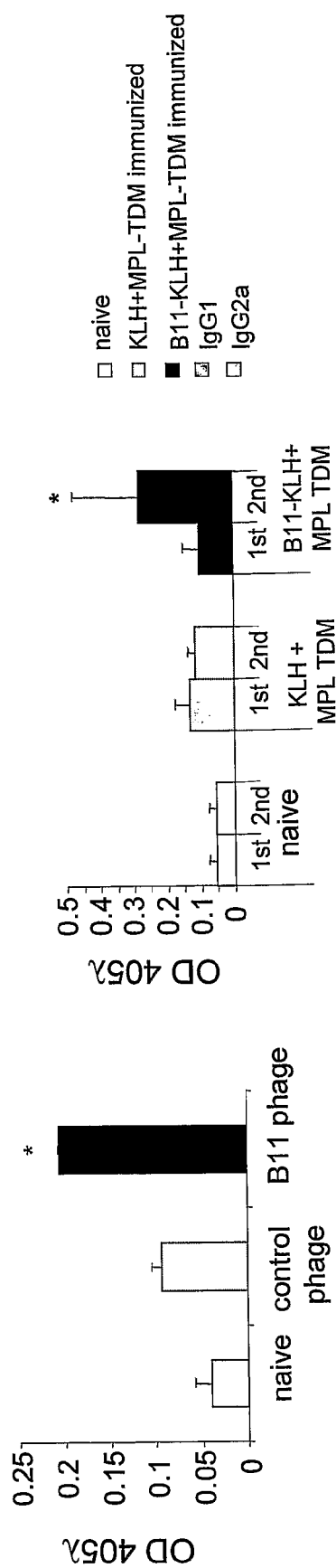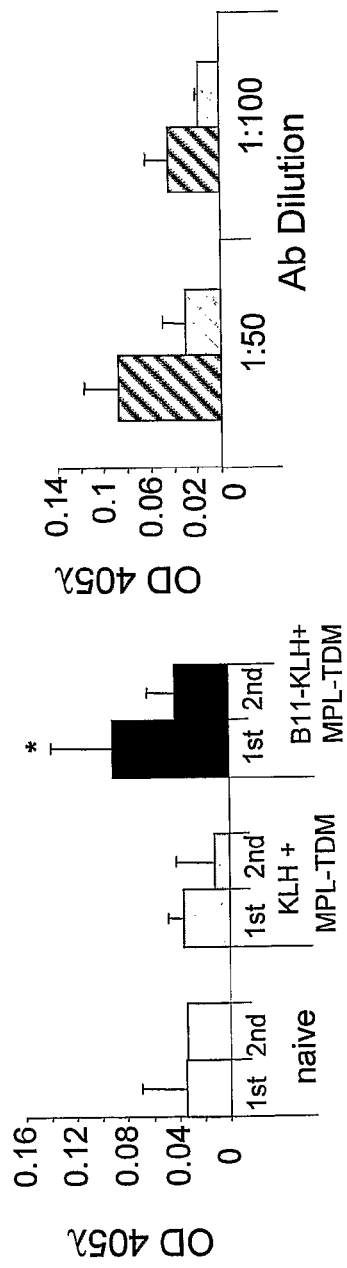

PEPTIDE MIMOTOPES OF MYCOBACTERIAL MANNOSYLATED LIPOGLYCANS AND USES THEREOF

This is a National Phase Application filed under 35 U.S.C. 371 as a national stage of PCT/IL05/00199, filed Feb. 17, 2005, an application claiming the benefit under 35 U.S.C. 119(e) U.S. Provisional Application No. 60/545,510, filed Feb. 19, 2004, and claiming the benefit under 35 U.S.C. 119(e) U.S. Provisional Application No. 60/582,221, filed Jun. 24, 2004, the entire content of each of which is hereby incorporated by reference in its entirety.

FIELD OF THE INVENTION

This invention relates to novel amino acid molecules that mimic epitopes (mimotopes) of mycobacterial mannosylated lipoglycans such as lipoarabinomannan (ManLAM) and induce an immune response to ManLAM and their use in diagnosis and immunization against mycobacterial infections.

LIST OF PRIOR ART

The following is a list of prior art considered to be relevant to the subject matter of the present invention:
Chatterjee, D., et al. *J Biol Chem* 267: 6234-6239 (1992);
Prinzis, S., et al. *J Gen Microbiol* 139: 2649-2658 (1993);
Nigou, *J. Biochimie* 85:153-166 (2003);
Hetland G, et al. *Clin Diagn Lab Immunol.* 5(2):211-8 (1998);
Antunes A, et al. *Res Microbiol.* 153(5):301-5 (2002);
Glatman-Freedman A., *FEMS Immunol Med Microbiol.* 39(1):9-16 (2003).
Hamasur B, et al., *Vaccine* 16:17(22):2853-61 (1999);
Luo P., et al. *J Biol Chem.*; 275(21):16146-54 (2000);

BACKGROUND OF THE INVENTION

Tuberculosis (TB) is mostly a pulmonary lung disease caused by *Mycobacterium tuberculosis* (Mtb). This organism is a slow-growing bacillus that is transmitted by the respiratory route. Soon after infection, the bacilli penetrate alveolar macrophages and survive within early phagosomes. Innate immune responses directed by macrophages predominate early in the infection. Subsequent recruitment of dendritic cells leads to cell-mediated responses involving $CD4^+$ and $CD8^+$ T cells and eventually to granuloma formation. Among infectious diseases, tuberculosis remains the second leading killer of adults in the world, with more than 2 million TB-related deaths each year (CDC 2004). The vast majority of immunocompetent individuals are able to contain, but not eliminate, the pathogen in pulmonary granulomas, leading to latent tuberculosis infection a small minority of cases, through unclear mechanisms, persistent bacilli can reactivate to produce disease many years to decades after initial infection.

Virulent *Mycobacterium* Cell Wall-associated Lipoglycans

A major cell surface component of Mtb and other virulent *Mycobacterium* sp. is the polysaccharide mannosylated lipoarabinomannan (ManLAM). ManLAM is a phosphatidylinositol-anchored lipoglycan composed of a mannan core with oligoarabinosyl-containing side-chains with diverse biological activities. This polysaccharide accounts for up to 5 mg g −1 bacterial weight. ManLAM structure differs according to mycobacterial species, and three general classes of LAM have been described: (i) ManLAM, from the virulent strains Erdman and H37Rv and the avirulent strains H37Ra and BCG [Chatterjee, D., et al. *J Biol Chem* 267: 6234-6239 (1992); Prinzis, S., et al. *J Gen Microbiol* 139: 2649-2658 (1993)], which is characterized by extensive mannose capping of the arabinan termini; (ii) phospho-myo-inositol-capped LAM (PILAM), found in the rapidly growing mycobacteria *M. smegmatis* and *M. fortuitum* [Nigou, *J. Biochimie* 85:153-166 (2003)]; and (iii) AraLAM, which was described in the rapidly growing *M. chelonae* and lacks mannosylation in its arabinan termini [Guerardel, Y., et al. *J Biol Chem* 277:30635-30648 (2002)]. Although there is significant heterogeneity between LAM molecules with respect to glycosylation and acylation [Nigou et al. (2003) ibid.], differences in biological activity between the major classes of LAM have been attributed primarily to the heavy mannose capping of ManLAM [Chatterjee et al. (1992). ibid.]

In several publications it has been shown that sera of TB patients contain higher levels of anti-ManLAM antibodies than that of healthy individuals [Hetland G, et al. *Clin Diagn Lab Immunol.* 5(2):211-8 (1998)]. Consequently it has been suggested to be one of the candidate antigens for rapid diagnosis of TB [Antunes A, et al. *Res Microbiol.* 153(5):301-5 (2002)].

LAMs that are surface components have been suggested as target molecules for an efficient vaccine candidate due to its presence on the bacterial surface [Glatman-Freedman A, *FEMS Immunol Med Microbiol.* 39(1):9-16 (2003)] Nonetheless, purified ManLAM was found to be a poor immunogen [Hamasur B, et al., *Vaccine* 16:17(22):2853-61 (1999)]. It has been suggested to conjugate mycobacterial polysaccharides to a carrier protein [Glatman-Freedman A, (2003) ibid.].

SUMMARY OF THE INVENTION

The present invention is based on the identification, by screening through random phage display libraries, of several peptide-based mannosylated lipoarabinomannan (ManLAM) mimotopes. This group of peptides showed selective and direct binding to CS40 anti-ManLAM monoclonal antibody, while no binding to antibodies against other, non-mannosylated, mycobacterial lipoglycans, and competitive binding, vs. ManLAM, to CS40 anti-ManLAM antibody. They were also bound by IgG antibodies in sera of TB patients and Mtb experimentally infected mice, thus higher titers were measured in diseased patients and animals when compared to healthy immunized and non-immunized individuals and to naive mice. In addition, the tested peptides were capable of eliciting production of ManLAM-binding antibodies in vivo.

Thus, it has been envisaged that these novel peptide-based mimotopes and the like, may serve as potential amino acid based probes for diagnosis of mycobactarial infections in subjects characterized by the presence of ManLAM binding antibodies in the subjects, as well as for immunization of subjects against such mycobacterial infections. It should be noted that the term "mimotope" [Meloen R. et al. *J. Mol. Recognit.* 13:352-359 (2000)] is also known in the art by the terms "mimitope" [Arnold G. et al. *Intervirology* 39:72-78 (1996)]; "mimotypes" [Benhar I. *Biotechnol. Adv.* 19:1-33 (2001)]; "mimetics" [Vyas et al. *Proc. Natl. Acad. Sci.* USA 100:15023-15028 (2003)] and refers to a compound that mimics the structure of an epitope and provokes an identical antibody response. The compound may be of the same or of a different type of molecule as the original epitope.

Thus, according to a first of its aspects, the present invention provides an amino acid molecule comprising a peptide comprising at least one of the following characteristics:

(a) being capable of binding to ManLAM binding antibodies;
(b) being capable of eliciting production of ManLAM binding antibodies.

The invention also provides a method for diagnosing a mycobacterial infection in a subject by determining the presence of ManLAM binding antibodies in a sample from said subject, the method comprising:
(i) contacting said sample with an amino acid molecule as defined above;
(ii) determining binding of said amino acid molecule to ManLAM binding antibodies;
wherein a positive determination indicates mycobacterial infection in the subject.

Within this diagnostic aspect of the invention, there is also provided a kit for diagnosing mycobacterial infection in a subject, the kit comprising an amino acid molecule as defined above.

In light of the immunostimulating effect of the amino acid molecules, the invention also provides a vaccine comprising as active agent the amino acid molecule as defined herein, together with a physiologically acceptable carrier.

According to this aspect of the invention there is also provided a method of immunizing a subject to mycobacterial infection, the method comprises providing said subject with an immunizing amount of an amino acid molecule as defined herein.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 2A-2D are bar graphs showing ManLAM-binding antibodies produced in B11 immunized mice: IgG in phage immunized mice (FIG. 1A) IgM (FIG. 1B) IgG (FIG. 1C) and IgG isotypes (FIG. 1D) in synthetic, KLH-peptide immunized mice.

DETAILED DESCRIPTION OF THE INVENTION

Figures 1A, 1B:
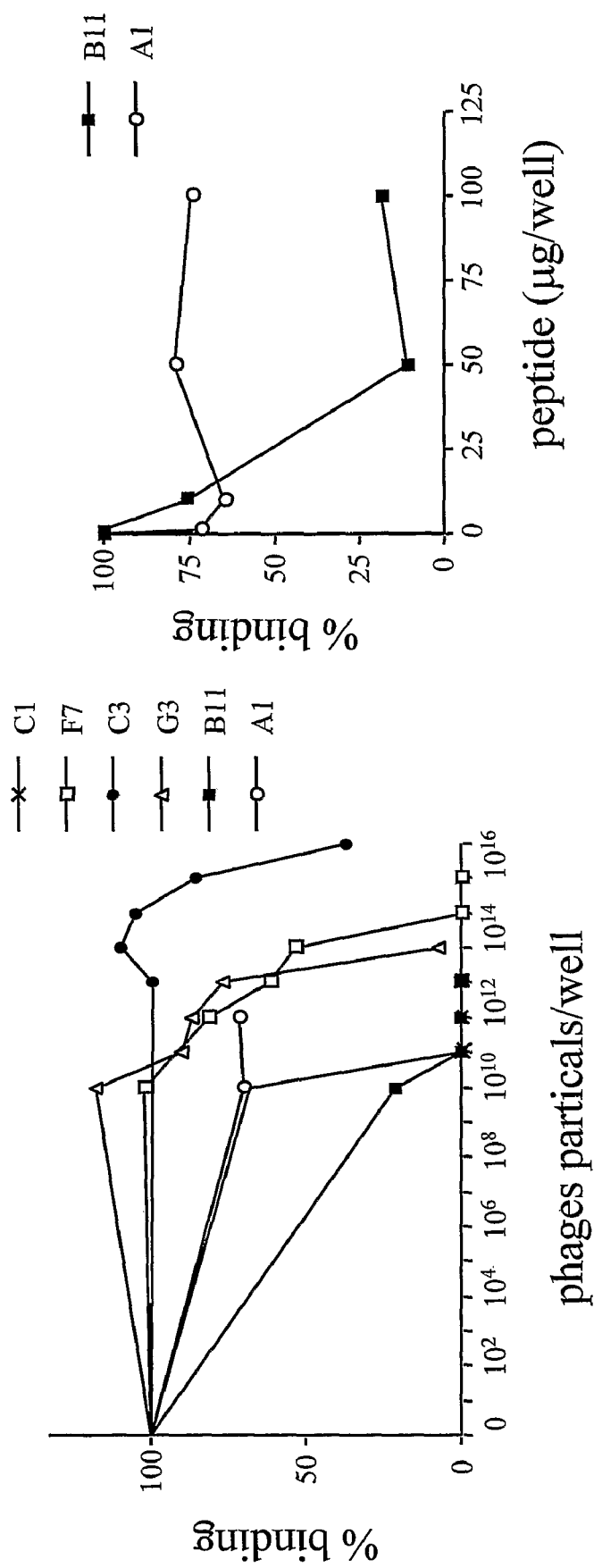
FIGS. 1A-1B are graphs showing competitive binding (% binding) vs. ManLAM of phage clones presenting different peptides (FIG. 1A) or of synthetic peptides B11 and A1 (FIG. 1B) to CS40 anti-ManLAM monoclonal antibody.

The present invention is based on the discovery, by phage display technology, of antigenic and immunogenic peptide-based mimicry of mannose-containing cell-wall compounds of *Mycobacterium tuberculosis*, specifically, mannosylated cell wall lipoglycan, such as ManLAM.

Thus, according to a first of its aspects, the invention provides an amino acid molecule comprising a peptide comprising at least one of the following characteristics:
(a) being capable of binding (selective binding, direct binding and/or competitive binding) to ManLAM binding antibodies;
(b) being capable of eliciting production of ManLAM binding antibodies.

The term "binding" as defined above refers to at least one of "selective binding", "direct binding" and "competitive binding" (see bellow). In accordance to the preferred embodiment of the invention this term refers to selective, direct and competitive binding.

"Selective binding" denotes binding of the amino acid molecule or the phage presenting the amino acid molecule, to ManLAM binding antibodies while not binding, at least at a detectable level as determined by methods hitherto known in the art, to antibodies directed to low- and non-mannosylated polysaccharides.

"Direct binding" denotes the binding of the amino acid molecule directly to the antigen binding portion of an antibody as determined for example by phage displaying the amino acid molecule immobilized onto a solid surface such as an ELISA plate or a nitrocellulose membrane and then testing for binding thereof to the antigen binding site of an antibody, either mAb or antibodies in sera of mycobacterial infected subjects.

"Competitive binding" denotes the dose dependant inhibition of the binding of antibodies (such as CS40 antibodies) to ManLAM by the amino acid molecule or phage displaying the amino acid molecule.

The term "ManLAM binding antibodies" as used herein denotes monoclonal antibodies (mAb) as well as polyclonal antibodies which bind to ManLAM. Preferably, such antibodies bind to lipoglycan carrying relatively high level of mannose residues, such as ManLAM, lipomannan (LM) and arabinomannan (AM). It is preferable that the antibodies bind at least to ManLAM.

Binding efficacy of the amino acid molecule to ManLAM binding antibodies may be evaluated by determining the magnitude of OD decrease when serial dilutions of phage clones/amino acid molecule are incubated with CS40 mAb. The phage clones/amino acid molecule with a higher affinity to mAb will show maximum inhibition of the binding of the mAb to ManLAM with the lowest number of phage particles or lowest amount of amino acid molecule, respectively.

The amino acid molecule according to the invention and in particular, the peptide forming part of the amino acid molecule, may comprise naturally occurring amino acids, semi-synthetic amino acids as well as synthetic amino acid sequences.

The term "naturally occurring amino acid" refers to a moiety found within a peptide and is represented by —NH—CHR—CO—, wherein R corresponds to the side chain of the 20 naturally appearing amino acids.

Nonetheless, the peptide of the invention may also comprise non-naturally occurring amino acids.

The term "non-naturally occurring amino acid" (amino acid analog) is either a peptidomimetic, or is a D or L residue having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. This term also refers to the D-amino acid counterpart of naturally occurring amino acids. Amino acid analogs are well known in the art; a large number of these analogs are commercially available. Many times the use of non-naturally occurring amino acids in the peptide has the advantage that the amino acid molecule is more resistant to degradation by enzymes which fail to recognize them.

A further characteristic of the amino acid molecule of the invention is that it binds to antibodies which have specificity to mannose containing polysaccharide. This is evident from their binding to anti-ManLAM antibodies vs. their lack of binding to antibodies directed against polysaccharides which do not have mannose residues, such as to CS35 anti-LAM mAb, 735 anti-ploy α(2→8) N-acetyl neuraminic acid mAb, and 2H1 anti-glucuronoxylomannan mAb.

In order to determine whether an amino acid sequence falls within the scope of the invention one of the following assays should be determined:

Assay 1: Binding to ManLAM Antibodies:

(a) The selectivity of binding of a candidate sequence by one option may be examined by binding to the CS40 mAbs against ManLAM while not binding to other anti-polysaccharide mAbs such as CS35 anti-LAM, 735 anti-poly alpha N-acetyl neuraminic acid mAb and 2H1 anti-glucronoxylomannam mAb-as described in the detailed description part of the application.

(b) By another option the competitive binding candidate amino acid molecule may be determined based on the dose dependent inhibition of the binding of Abs to ManLAM by the candidate amino acid molecule.

(c) By yet another option, direct binding may be determined based on direct binding measurements, i.e. determination of ManLAM antibodies, both monoclonal antibodies and antibodies from individuals' sera exposed to mycobacterial infection to the amino acid molecule. The direct binding measurements is based on the fact that antibodies level from mycobacterial infected subjects is higher that the level thereof, if at all, in healthy subjects (vaccinated or healthy, non-vaccinated).

The candidate will have one or more of the above binding properties preferably all three.

Assay 2: Eliciting an Immune Response

According to this assay, a candidate amino acid molecule is preferably conjugated to a carrier protein and injected to a test animal (in accordance with the procedure in the detailed description part). The serum of the immunized animal is tested for the capacity to produce specific ManLAM binding antibodies (e.g. IgG, IgA or IgM) as demonstrated in serological tests.

Candidate amino acid molecules that were active in one of the assays above fall under the scope of the present invention.

Based on phage display technology six dodecamer peptides were identified (generally referred to herein as the original amino acid molecules). These peptides are depicted in the following Table 1:

TABLE 1

ManLAM peptide mimotopes

| Clone | Amino acid sequence | |
|-------|---------------------|---|
| A1 | WEADDKNQHGEG | (SEQ ID NO: 6) |
| B11 | ISLTEWSMWYRH | (SEQ ID NO: 1) |
| C1 | EEGPWSTHVGRT | (SEQ ID NO: 2) |
| C3 | WGNEGGDHLQPV | (SEQ ID NO: 3) |
| F7 | SLKIRWELKMYQE | (SEQ ID NO: 4) |
| G3 | AVERWEKHTWSE | (SEQ ID NO: 5) |

*The postulated motif amino acids are indicated in gray box and bold letters

Optimal alignment of the above peptides (as described in the Materials and Methods) identified a motif marked in the above Table 1 in gray.

Interestingly, an internal aromatic amino acid residue was identified in all these dodeca-peptides. This finding is in correlation with previous evidence suggesting that aromatic residues are critical in peptide sequences that mimic surface conformations specifically recognized by sugar binding ligands. [Luo P et al. *J Biol Chem.;* 275(21):16146-54. (2000)]. Further, in some of these peptides, more than one internal aromatic residue was present. For example, B11 comprises two tryptophan and one tyrosine internal residues (SEQ ID NO: 7, . . . WSMWY . . . ), and F7 and G3 both comprise two aromatic residues (SEQ ID NO: 8, . . . WELKMY . . . and SEQ ID NO: 9: . . . WEKHTW . . . , respectively). Thus, according to one aspect, the amino acid molecules according to the invention comprise one or more internal aromatic residues.

Another interesting observation from the above alignment is that an internal aromatic amino acid residue has an adjacent, typically, although not necessarily, preceding hydrophilic amino acid residue such as glutamate (E), proline (P), arginine (R).

According to the invention, the amino acid molecule may comprise one or more copies of the same peptide (monoepitopic peptide constructs) or different peptides (multiple antigenic peptide constructs) and immunological modifications of the above identified peptides. The amino acid molecules may be linked to carrier proteins, all as defined herein below.

The "internal aromatic amino acid residue" includes a naturally occurring and non-naturally occurring amino acid residue carrying an aromatic side chain, the residue being flanked from the amino as well as from the carboxylic termini thereof by at least on residue (which may naturally occurring, non-naturally occurring or peptidomimetic organic moiety, all being as defined herein). For instance, the internal aromatic tryptophan identified in the above peptides may be replaced with one of the naturally occurring aromatic residues, Phenylalanine (F), Histidine (H), Tryptophan (W), Tyrosine (Y) and conservative substitutions thereof, as long as the immunological character of the molecule is retained.

The term "immunologic modification" according to the invention includes any one of the following: substitution of one or more amino acid residues, deletion of one or more amino acid residues, insertion of one or more amino acid residues, chemical modification of one or more amino acid residues, as well as other modifications known in peptidobased technologies, all of which resulting in an amino acid molecule which retains the immunologic character of the original amino acid molecule from which it is derived.

The term "immunologic character" concerns both the antigenic character (i.e. the capacity to bind ManLAM binding antibodies), as well as the immunogenic character (i.e. the capacity to elicit, upon immunization, production of ManLAM binding antibodies) of the original amino acid molecule.

Modification also includes alteration of a bond within the peptidic backbone, i.e. that the bond between the N— of one amino acid residue to the C— of the next has been altered to non-naturally occurring bonds by reduction (to —$CH_2$—NH—), alkylation (methylation) on the nitrogen atom, or the bonds have been replaced by amidic bond, urea bonds, or sulfonamide bond, etheric bond (—$CH_2$—O—), thioetheric bond (—$CH_2$—S—), or to —CS—NH—; The side chain of the residue may be shifted to the backbone nitrogen to obtain N-alkylated-Gly (a peptidoid).

Modification also includes cyclization of the amino acid molecule, e.g. by forming S—S bonds. S—S bonds may be formed via the inclusion of sulphor-containing amino acid residues, such as cysteine at each terminus of the amino acid molecule. Cyclic peptides have been shown to be more stable and with higher biological activity than the corresponding linear molecule [Tibbetts S. et al. *Peptides*. 21(8)1161-7 (2000)].

"Substitution" includes the replacement of one or more amino acid residues either by other naturally occurring amino acids, (conservative and non-conservative substitutions), by non-naturally occurring amino acids (conservative and non-conservative substitutions), or with organic moieties which serve either as true peptidomimetics (i.e., having the same steric and electrochemical properties as the replaced amino acid), or merely serve as spacers in lieu of an amino acid, so as to keep the spatial relations between the amino acid spanning this replaced amino acid.

The term "conservative substitution" in the context of the present invention refers to the replacement of an original amino acid present in the identified amino acid molecules with a naturally or non-naturally occurring amino or a peptidomimetic residue having similar steric properties. Where the side-chain of the original amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid). However where the original amino acid to be replaced is charged, the conservative substitution according to the definition of the invention may be with a naturally occurring amino acid, a non-naturally occurring amino acid or a peptidomimetic moiety which are charged, or with non-charged (polar, hydrophobic) amino acids that have the same steric properties as the side-chains of the replaced amino acids. The purpose of such a procedure of maintaining the steric properties but decreasing the charge is to decrease the total charge of the compound, for example for improving its membrane penetrating properties.

For example in accordance with the invention the following substitutions are considered as conservative: replacement of arginine by cytroline; arginine by glutamine; aspartate by asparagine; glutamate by glutamine.

As the naturally occurring amino acids are grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

The following are some non-limiting examples of groups of naturally occurring amino acids or of amino acid analogs are listed bellow. Replacement of one member in the group by another member of the group will be considered herein as conservative substitutions:

Group I includes leucine, isoleucine, valine, methionine, phenylalanine, serine, cysteine, threonine and modified amino acids having the following side chains: ethyl, n-butyl, —$CH_2CH_2OH$, —$CH_2CH_2CH_2OH$, —$CH_2CHOHCH_3$ and —$CH_2SCH_3$. Preferably Group I includes leucine, isoleucine, valine and methionine.

Group II includes glycine, alanine, valine, serine, cysteine, threonine and a modified amino acid having an ethyl side chain. Preferably Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, CO—NH-alkylated glutamine or asparagine (e.g., methyl, ethyl, n-propyl and iso-propyl) and modified amino acids having the side chain —$(CH_2)_3COOH$, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, glutamine, asparagine, methyl aspartate, ethyl aspartate, benzyl aspartate and methyl glutamate, ethyl glutamate and benzyl glutamate.

Group V includes histidine, lysine, arginine, N-nitroarginine, β-cycloarginine, μ-hydroxyarginine, N-amidinocitruline and 2-amino-4-guanidinobutanoic acid, homologs of lysine, homologs of arginine and ornithine. Preferably, Group V includes histidine, lysine, arginine, and ornithine. A homolog of an amino acid includes from 1 to about 3 additional methylene units in the side chain.

Group VI includes serine, threonine, cysteine and modified amino acids having C1-C5 straight or branched alkyl side chains substituted with —OH or —SH. Preferably, Group VI includes serine, cysteine or threonine.

The term "non-conservative substitutions" concerns replacement of one or more amino acid residues present in the original molecule by another naturally or non-naturally occurring amino acid, having different a different size, configuration and/or electronic properties compared with the amino acid being substituted. Thus, the side chain of the substituting amino acid can be significantly larger (or smaller) than the side chain of the original amino acid being substituted and/or can have functional groups with significantly different electronic properties than the amino acid being substituted.

According to the invention modification may also involve non-conservative substitutions, as long as that the immunological activity of the amino acid molecule is retained.

"Peptidomimetic organic moiety" can be substituted for amino acid residues in the molecules of the invention both as conservative and as non-conservative substitutions. The peptidomimetic organic moieties often have steric, electronic or configurational properties similar to the replaced amino acid.

Peptidomimetics are often used to inhibit degradation of the amino acid molecules by enzymatic or other degradative processes. The peptidomimetics can be produced by organic synthetic techniques. Examples of suitable peptidomimetics include D amino acids of the corresponding L amino acids, tetrazol [Zabrocki et al., *J. Am. Chem. Soc.* 110:5875-5880 (1988)]; isosteres of amide bonds [Jones et al., Tetrahedron Lett. 29: 3853-3856 (1988)]; LL-3-amino-2-propenidone-6-carboxylic acid (LL-Acp) [Kemp et al., *J. Org. Chem.* 50:5834-5838 (1985)]. Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., *J. Org. Chem.* 54:109-115 (1987). Other suitable peptidomimetics are shown in Nagai and Sato, Tetrahedron Lett.

26:647-650 (1985); Di Maio et al., *J. Chem. Soc. Perkin Trans.*, 1687 (1985); Kahn et. al., Tetrahedron Lett. 30:2317 (1989); Olson et al., *J. Am. Chem. Soc.* 112:323-333 (1990); Garvey et al., *J. Org. Chem.* 56:436 (1990). Further suitable peptidomimetics include hydroxy-1,2,3,4-tetrahydroisoquinoline-3-carboxylate (Miyake et al., *J. Takeda Res. Labs* 43:53-76 (1989)); 1,2,3,4-tetrahydro-isoquinoline-3-carboxylate [Kazmierski et al., *J. Am. Chem. Soc.* 133:2275-2283 (1991)]; histidine isoquinolone carboxylic acid (HIC) [Zechel et al., *Int. J. Pep. Protein Res.* 43 (1991)]; (2S,3S)-methyl-phenylalanine, (2S, 3R)-methyl-phenylalanine, (2R, 3S)-methyl-phenylalanine and (2R,3R)-methyl-phenylalanine [Kazmierski and Hruby, Tetrahedron Lett. (1991)].

"Deletion" includes exclusion of one or more amino acid residues (naturally occurring, non-naturally occurring, or peptidomimetic organic moiety) as compared to the original molecule from which it is derived.

"Insertion" or "addition" includes the addition of one or more amino acid residues (naturally occurring, non-naturally occurring, or peptidomimetic organic moiety) as compared to the original molecule from which it is derived.

"Chemical modification" includes modification at the side chain of the amino acid residue, as well as modification of the peptidic bond. Accordingly, a functional group may be added to the side chain, deleted from the side chain or exchanged with another functional group. Typically, the modifications are conservative modifications resulting in conservative substitution. Examples of conservative modifications of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine.

Other chemical modifications known in the art include arboxymethylation, acylation, phosphorylation, glycosylation or fatty acylation, and others.

According to the invention, the modification should be an immunological modification, i.e. such that the antigenic binding characteristic or the immunostimulatory effect of the modified amino acid molecule (i.e. the immunogenecity) is substantially retained as compared to the original amino acid molecule from which they are derived.

"Carrier proteins" are known in the art. It is acceptable that small molecules such as drugs, organic compounds, and peptides and oligosaccharides with a molecular weight of less than 2-5 kDa are less immunogenic, even when administered in the presence of adjuvants. In order to generate an immune response to these compounds, they are typically attached to a carrier protein or other carrier compound that is immunogenic. The conjugation of the carrier protein to the amino acid molecule of the invention may result in stimulation of an immune response to the peptide (cellular as well as humoral response) as well as in an increase in the intensity of the immune response to the peptide [Jacobson R M, et al. *Minerva Pediatr.* 54(4):295-303 (2002)].

Non-limiting examples of carrier proteins which may be utilized according to the invention include Keyhole limpet hemocyanin (KLH); Bovine serum albumin (BSA); Rabbit serum albumin (RSA); Ovalbumin (OVA); Pumpkin Seed Globulin (PSG), tetanus toxoid (TT), diphtheria toxin (CRM).

Other carrier proteins which may be utilized in accordance with the invention include dentritic polymers (dendrimers, dendrons and hyperbranched dendritic polymers) which are synthetic, three-dimensional macromolecule. The dendritic polymers are built up from monomers, with new branches added in steps until a tree-like structure is created. When using dendritic polymers as a carrier, multiple copies of the same or different amino acid molecule according to the invention may be conjugated to each branch of the tree-like structure.

According to one preferred embodiment, the amino acid molecule comprises B11 peptide (ISLTEWSMWYRH, SEQ ID NO:1), and conservative modifications thereof. One example of a conservative modification includes the replacement of Try (W) with another aromatic amino acid residue, such as Phe (F), His (H) or Tyr (Y).

The peptides identified above and which form part of the amino acid molecule according to the invention bind with specificity to ManLAM binding antibodies, preferably to anti-ManLAM antibodies.

As described hereinabove, ManLAM is a major cell surface component of virulent *Mycobacterium* sp. In several publications it has been shown that sera of Tuberculosis patients contain higher levels of ManLAM binding antibodies than that of healthy individuals [Hetland G, et al. (1998) ibid.].

Thus, according to the invention there is provided a method for diagnosing a mycobacterial infection in a subject by determining the presence of ManLAM binding antibodies in a sample from said subject. According to one embodiment, the ManLAM binding antibodies are anti-ManLAM antibodies. The diagnostic method of the invention comprises contacting the sample with the amino acid molecule and determining formation of a complex between the amino acid molecule and ManLAM binding antibodies. The formation of such a complex indicating that said subject is or has been infected by a mycobacterial agent.

In the context of the present invention the term "subject" denotes mammal subjects, including humans and non-human animals, such as cattle, sheep, deers, dogs, cats etc.

"Sample" denotes a fluid bodily sample, preferably a blood sample (including whole blood or blood's serum) or a bodily secretion, e.g. urine, saliva, phlegm etc.

The method of the present invention may be by binary (yes/no) determination of the presence of ManLAM binding antibodies in the serum.

However it was also surprisingly found that the amino acid molecules of the invention are capable of distinguishing between individuals having acute infection of TB and individuals immunized for TB. This finding leads the way to a method of determining active infection of TB (as compared to existence of anti-TB antibodies present in the individual as a result from prior immunization) by the determination of the levels of the complexes between the amino acid of the invention and antibodies.

Thus the present invention concerns a method for determining whether a subject has active mycobacterial infection, the method comprising:

(a) contacting a sample from said subject with an amino acid molecule comprising a peptide comprising at least one of the following characteristics:
  i) being capable of binding to ManLAM-binding antibodies;
  ii) being capable of eliciting, upon immunization in a subject, production of ManLAM binding antibodies.
(b) determining level of complexes comprising said amino acid molecule and ManLAM binding antibodies;
(c) comparing said level to a standard, a level higher than said standard indicating active myobacterial infection in the subject.

The determination may be by comparing the level of complexes formed in a sample from a tested individual, to a pre-defined standard (threshold) obtained by determining the level of complexes in clinically diagnosed active TB patients as compared to individual immunized with TB but not actively ill.

The standard is a level wherein above it the person has a statistically significant probability of falling under the TB-ill patients group and bellow it has a statistically significant probability of falling under TB-immunized individuals (although there may be overlap between the actual levels). The standard may be determined by statistical methods known in the art.

"Standard" denotes either a single standard value or a plurality of standards with which the level of ManLAM binding antibodies from the tested sample is compared. The standards may be provided, for example, in the form of discrete numeric values or is colorimetric in the form of a chart with different colors or shadings for different levels of antibodies; or they may be provided in the form of a comparative curve prepared on the basis of such standards. The standards may be prepared by determining the level of antibodies present in samples obtained from a plurality of subjects. For example, the standards may be determined by the level of antibodies in positive and negative *Bacillus Calmette-Guerin* (BCG) vaccinated subjects and non-vaccinated healthy subjects.

The determination step may be performed using any of the technologies available in the art. Non-limiting examples include visualization of the bound amino-acid molecule-antibodies by the use of the relevant label conjugated secondary antibody (e.g. molecular probes) which may be fluorescent, enzyme-linked to give a colorimetric reaction (by enzyme-linked immunosorbent assay (ELISA)), radioimmunoassay (RIA), by the use of a fluorescently labeled affinity purification of the antibodies, (relevant to testing of cultures), FACS analysis, Dot-Blot, confocal laser scanning microscopy (CLSM).

The determination step may also include the visualization of the bound amino-acid molecule-antibodies by agglutination methods, e.g. by the use of latex beads having immobilized onto their surface the amino acid molecules of the invention; or by any other means, as known to those versed in the art.

In addition, it is possible by the method of the invention to determine treatment efficacy by following the level of Man-LAM binding antibodies in a sample from a subject undergoing treatment for a mycobacterial infection. The method comprises the steps of:
 (a) obtaining samples from said subject, from at least two discrete time points, and contacting the samples with an amino acid molecule comprising a peptide comprising at least one of the following characteristics:
  i) being capable of binding to ManLAM-binding antibodies;
  ii) being capable of eliciting, upon immunization in a subject, production of ManLAM binding antibodies.
 (b) determining level of complexes comprising said amino acid molecule and ManLAM binding antibodies in said samples;
 wherein a difference in the level between the two time points is indicative of the effectiveness of the treatment.

The time points may be before, during and after the treatment. For example, a first sample may be taken at a time point prior to initiation of the treatment and a second sample may be taken at a time point after the treatment. A decrease in the level of complexes in the second sample as compared to the first sample would be indicative that the treatment is effective.

In another example, a first sample may be taken at a time point during the treatment and a second sample may be taken at a time point after the treatment. A decrease in the level of the complexes in the second sample as compared to the first sample would also be indicative that the treatment is effective.

This method is based on earlier evidence showing that levels of anti-Glycolipid antibodies change post treatment [Maekura, R., et al., *J Clin Microbiol.* 39(10):3603-8 (2001)].

According to one embodiment, the mycobacterial infection is an infection caused by *Mycobacterium tuberculosis* (Mtb), *Mycobacterium africanum* or *Mycobacterium bovis* (the tuberculosis complex), or by *Mycobacterium leprae*.

According to a preferred embodiment the mycobacterial infection is an infection caused by *Mycobacterium tuberculosis*, thereby causing Tuberculosis.

The invention also provides a diagnostic assay kit for diagnosing mycobacterial infection in a subject, the kit comprising one or more amino acid molecule according to the invention. As typical for medical or diagnostic use, the kit may also comprise instructions for use of the amino acid molecule for diagnosing the infection. The kit may also comprise other diagnostic components, such as the substrate onto which the amino acid molecule is immobilized (e.g. for ELISA), secondary antibodies (labeled) etc.

The specific experimental results presented herein provide evidence that the amino acid molecules of the invention are capable of eliciting production of antibodies which bind to ManLAM (specific, direct as well as competitive binding). Since ManLAM is a unique fingerprint for *Mycobacterium* sp. it may also be used as a vaccine for immunizing subjects against such infectious agents.

Thus, the invention also provides a vaccine comprising an immunologically acceptable carrier and as an active agent amount of an amino acid molecule according to the invention. The amount of the amino acid molecule is determined such that an immunological response is produced upon administration of the vaccine to the subject.

"Immunological response" in the context used herein denotes the production of a protective immune response. Particularly, that the immune response evoked by the amino acid molecule in question protects the subject immunized from contracting a mycobacterial infection, or that the immune response evoked by the amino acid molecule at least confers a substantially increased resistance to infections with mycobacteria. The immune response preferably includes the generation of antibodies that bind to mannosylated glycans, with preference to ManLAM.

The vaccine may also include immunologically acceptable adjuvants. Accordingly, immunization may be carried out in combination with whole phage particles [Benhar I., *Biotechnol Adv* 19:1-33 (2001); Alum; Monophosphoryl lipid A (MPL), CpG Islands, Saponins, cytokines, as well as commonly known antigen delivery vehicles, such as emulsions, micro-particles, iscoms, liposomes, virosomes and virus like particles [Singh M and Srivastava I. *Curr HIV Res.* 1(3):309-20 (2003)].

The amount of the amino acid molecule in the vaccine is determined by such considerations as may be known in the art. The amount must be effective to achieve the desired immunological response as described above, i.e. production of antibodies which bind to ManLAM to a level sufficient to achieve protection against a threatening infection. This effective amount is typically determined in appropriately designed trials (e.g. dose range studies) and the person versed in the art will know how to properly conduct such trials in order to determine the effective amount. Some considerations for determining the effective amount include the clinical condition of the subject, the site and method of administration, scheduling of administration, patient age, sex, body weight and other factors known to medical practitioners.

The vaccines are administered in a manner compatible with the dosage formulation, and in such amount as will be immunogenic. The quantity to be administered depends on the subject to be treated, including, e.g., the capacity of the individual's immune system to mount an immune response, and the degree of protection desired. Suitable regimes for initial administration and booster shots are also variable but are typified by an initial administration followed by subsequent inoculations or other administrations.

The vaccine may comprise one or more amino acid molecules of the invention, or alternatively, the amino acid molecule may comprise multiple copies of the same or different peptides as defined hereinabove. A preferred vaccine is such that the amino acid molecule comprises a carrier protein linked to one or more peptides as defined herein.

According to one embodiment, the vaccine is administered to the subject in need by means of parenteral administration, e.g. intravenously (i.v.), intradermally (i.d.) intraperitoneally (i.p.), intramuscularly (i.m.), subcutaneous (s.c.), intranasal (i.n.), intrarectally as well as by oral route or by inhalation.

The invention also provides a method of immunization of a subject against mycobacterial infection; the method comprises providing said subject with an amount of an amino acid molecule as defined, the amount being sufficient to achieve effective immunity effect against infectious agents carrying mannose-containing cell-wall lipoglycans, such as ManLAM, LM and AM.

As will be appreciated by those versed in the art, the subject may be provided with a single dose or multiple doses of the immunogenic amino acid molecule of the invention. The multiple doses may be provided over an extended period of time in a single daily dose or in several doses a day. The doses and schedule of treatment is determined by considerations available to those known in the art.

SPECIFIC EXAMPLES

Materials and Methods

Biopanning of Phage Display Libraries

Phage display libraries were constructed in the fth1 type 88 vector [Enshell-Seijffers D, and Gershoni, J. M. epitopes, In *Current Protocols in Immunology*, Vol. 2. J. E. Coligan, ed. Wiley, New York. p. 9.8.1(2002)]; Stern, B., et al. Faseb J 11, 147-153 (1997)] at the laboratory of Prof. Gershoni (Department of Cell Research and Immunology, George S. Wise Faculty of Life Sciences, Tel Aviv University, Israel)

Biopanning of random phage display libraries was performed as described in Enshell-Seijffers and Gershoni [Enshell-Seijffers and Gershoni (2002), ibid.], based on the methods of Smith and Scott, [Smith, G. P., and Scott, J. K. *Methods Enzymol* 217:228-257 (1993)]. Briefly, 6-well polystyrene plates (Nunc, Roskilde, Denmark) were coated with mAbs (5 µg/well) in TBS and then blocked with TBS/0.25% gelatin for 2 h at RT. Phage particles ($1\times10^{11}$) in TBS/0.25% gelatin were bound to the mAb-coated wells at 4° C. for 16 h. The unbound phages were removed by 4 washes of TBS, and the bound phages were eluted by adding a glycine/HCl/BSA buffer, pH 2.2, for 10 min, which was then neutralized using Tris buffer, pH 9.1. Phages were amplified in *Escherichia coli* DH5α. For titer determination, aliquots of the eluate or the amplificate were plated in serial dilutions on Luria broth (LB) agar plates. Up to six biopanning rounds were performed Phage Clone Screening Assay and Peptide Sequencing Screening of the phage clones tested for recognition with the CS40 anti-ManLAM mAb was performed by the immuno Dot-Blot technique (Enshell-Seijffers D. et al., *J Mol Biol*, 334, (2003); Enshell-Seijffers and Gershoni, (2002) ibid.]. Briefly, the phage particles were bound directly to nitrocellulose membranes (Schleicher and Schuell GmbH, Dassel, Germany), which were then blocked with TBS/10% skim milk (1 h at RT). The anti-polysaccharide mAb was added (1 µg/ml) to the membranes and incubated overnight at 4° C. The membranes were then washed in TBS 5 times for 5 min at RT. The secondary antibody (HRP-conjugated goat anti-mouse IgG (Jackson Laboratories, West Grove, Pa.) diluted 1:5000 was then added (incubated for 1 h at RT). Positive clones were detected by Dot-Blot. ManLAM was used as a positive binding control. Phage clones that were determined to be positive by the Dot-Blot assay were retested by the same method in triplicate and by ELISA competition. In the selection of the phages with each of the Abs, a control phage clone was selected. These control phage clones did not bind the relevant mAb and did not present amino acids of the motif. The control phages were used as negative controls in binding and immunization assays.

Single-stranded DNA of the positive phage clones was isolated using the QIAprep Spin M13 Kit® (QIAGEN, Hilden, Germany). The DNA sequences encoding the peptide insert were analyzed at the Hebrew University, Jerusalem, Israel by an automated ABI 310 DNA sequencer (Perkin-Elmer, Santa Clara, Calif.). The deduced peptide sequences were aligned by ClustalW alignment using MacVector™ 7.0 (Oxford, UK). The anti-glucuronoxylomannan (GXM) mAb 2H1 was obtained from Prof. Casadaval (Albert Einstein College of Medicine, New York). The anti-MgB sugar mAb 735 was obtained from Prof. Bitter-Suermann (Institute of Medical Microbiology, Hannover, Germany). ManLAM from *M. tuberculosis* strain H37Rv, and anti-ManLAM mAb (CS40), were obtained from Drs. Brennan and Belisle (Colorado State University, Fort Collins, Colo.).

Direct Peptide and ManLAM ELISA Assays

Direct ELISA assays were performed by coating 96-well ELISA plates (O/N at 4° C.) with 5-20 µg peptide per well in PBS ManLAM 5 µg/well (50 µl/well). The plates were washed twice in phosphate buffered saline (PBS), blocked with PBS/1% BSA and then washed twice (PBS). Sera diluted in PBS/0.5% BSA (1:50 or 1:200) or CS40 mAb (1:2000) (50 µl per well) was added and incubated for 1 h at 37° C. After washing, alkaline phosphatase-labeled goat anti-mouse immunoglobulin (Sigma, St. Louis, Mo.) was added. Following 90-min incubation at 37° C., p-nitrophenyl phosphate (KPL, Gaithersburg, Md.) was added to the plates, and optical density was measured at 405 nm using ELISA reader (ELX-800UV, Bio-Tec instruments, Winooski, Vt.). In all ELISA procedures, samples were tested in triplicate.

Human sera samples, after appropriate Helsinki endorsement, were obtained from Dr. Rahav (Chaim Sheba Hospital, Ramat Gan, Israel), Dr. Spectre (Hadassah University Hospital, Jerusalem, Israel), and Prof. Marchal (Pasteur Institute, Paris).

ELISA Competition

ELISA competition assay was performed according to Kaur et al., [Kaur, D., et al. Microbiology 148:3049-3057 (2002)]. Briefly, plates were coated with 0.5 µg/well ManLAM. Plates were blocked as described above. The CS40 mAb (diluted 1:2000) was mixed with various concentrations of either phage particles in TBS/1% BSA ($0-1\times10^{18}$ particles/well) or peptides in PBS/1% BSA (0-200 µg/well). This solution was then transferred to the ELISA plates and incubated for 1 h at 37° C. After washing (PBS), the ELISA procedure was performed as described above. Samples were all tested in triplicate Phage Immunization Phage immunization was performed by subcutaneous (s.c.) injection to mice of the selected phage clones, $1 \times 10^9$-$1 \times 10^{13}$ phage particles/mouse, or a control phage (as described above) in MPL-TDM adjuvant system (Sigma). The mice were boosted with the same dose three weeks later. Three weeks after the last immunization, production of specific polysaccharide binding IgG Abs was assessed in sera obtained by bleeding the tail vein of the immunized mice.

Peptide Synthesis and Conjugation

Peptides were synthesized by a solid-phase technique. For binding assays, peptides corresponding to the phage clones (A1, B11) were synthesized with no additional amino acids. For immunization, the B11 peptide was synthesized with an additional cysteine residue at the amino terminus for conjugation to sulfhydryl-reactive KLH, performed according to manufacturer's instructions (Pierce, Rockford, Ill.)

Peptide synthesis was performed by Prof. Fridkin at the Weizmann Institute, Rehovot, Israel, and at the Interdepartmental Facility of the Hebrew University Faculty of Medicine, Jerusalem, Israel.

Peptide Immunization

B11 (5 μg and 50 μg) conjugated peptides were administrated to specific pathogen-free (SPF) female BALB/c mice, 5-8 weeks old, intraperitoneally (i.p.) or s.c. The mice were boosted with the same dose three weeks later. In the s.c. immunization route, various adjuvants were tested: KLH-conjugated peptide was emulsified in MPL-TDM adjuvant system (Sigma) or in incomplete Freund's adjuvant (IFA) (Sigma) according to manufacturer's instructions, or in dimethyldioctadecylammonium bromide (DDA) (Fluka, Buchs, Switzerland). Immunization i.p. was performed using the KLH-conjugated peptide emulsified in the MPL-TDM adjuvant system. In all immunization experiments, control groups were immunized with KLH in the relevant adjuvant with no peptide.

In all immunized groups production of Abs was tested in the sera. For this, mice were bled from the tail vein at three times: pre-immunization, two weeks after first administration, and three weeks after second administration. All experiments were performed in accordance with the regulations of the animal experimentation ethics committee of the Hebrew University-Hadassah Medical School.

Experimental *Mycobacterium Tuberculosis* Infection

SPF female BALB/c mice were inoculated i.v. in the tail vein with $5 \times 10^5$ CFU of *M. tuberculosis* strain H37Rv in 200 μl of saline (a kind gift from Prof. G. Marchal, Pasteur Institute, Paris). Thirty days (6 mice) and three months (4 mice) after Mtb infection the mice were bled and tested for the presence of IgG antibodies that bound ManLAM and B11 peptide. The sera of six uninfected mice were used as negative controls. All experiments were performed in accordance with the regulations of the animal experimentation ethics committee of the Hebrew University-Hadassah Medical School.

Cell Culture

The cell line RAW 264.7 obtained from the American Type Culture Collection was grown in Dulbecco's modified Eagle's medium (DMEM) supplemented with 10% FCS, 1% penicillin, 1% L-glutamine, 1% nonessential amino acids, and 1% pyruvate (Biological Industries, Beit Haemek, Israel) to an 80% confluent culture at 37° C. in an atmosphere enriched with 5% $CO_2$.

Confocal Microscopy of FITC-labeled B11 Peptide Binding to RAW 264.7 Cell Line

B11 peptide (50 μg) was conjugated to FITC (Biotium, Hayward, Calif.) as described by Sethi et al., [Sethi, K. K., et al. Cell Motil Cytoskeleton 52:231-241 (2002)]. For confocal microscopy, RAW 264.7 cells were grown in 8-well glass slides, Chamber Slide™ (Nunc), as described above. Cells were washed three times in cold PBS and incubated with the FITC-labeled mimotope for 5 min at 4° C. in serial dilutions of 1:2-1:100 in cold PBS. Slides were imaged immediately with a Zeiss 410 confocal laser scanning microscope.

FACS Analysis of FITC-labeled Mimotope Binding to RAW 264.7 Cell Line

RAW 264.7 cells were grown in a 250-ml flask, washed 3 times in cold PBS, and harvested. Cells were then incubated for 15 min at 37° C., with the FITC-labeled peptide diluted 1:50, then washed 3 times in cold PBS. The fluorescence levels of 10,000 cell counts were determined by FACS (Becton Dickinson, Franklin Lakes, N.J.) and analyzed by CELLQuest™ software. Assay of competitive binding between mannose and the FITC-labeled B11 peptide was performed according to Nguyen and Hildreth, [Nguyen, D. G., and Hildreth, J. E. Eur J Immunol 33:483-493 (2003)].

Results

Sequences Selection by Phage Display Technology

In the search for mimotopes of mannosylated lipoarabinomannan (ManLAM), a major cell surface component of virulent *Mycobacterium*, phage display libraries were screened with CS40, a mAbs obtained against ManLAM from *Mycobacterium Tuberculosis* (Mtb) [Chatterjee, D., et al., *J Biol Chem* 267:6234-6239, (1992)], as described in Material and Methods. CS40 was shown to bind mannosylated molecules ManLAM and arabinomannan (AM). The specific epitope bound by is not yet defined [Navoa, J. A., et al. *Clin Diagn Lab Immunol* 10:88-94 (2003)].

All selected phage clones were tested by Dot-Blot for specific binding to the anti-ManLAM CS40 mAb. All phage clones bound only to the CS40 mAb and not to three other anti-polysaccharide mAbs: CS35 anti-LAM mAb [Kaur et al. (2002). ibid.], 735 anti-ploy α(2→8) N-acetyl neuraminic acid mAb [Kibbelaar, R. E., et al. *J Pathol* 159:23-28 (1989)], and 2H1 anti-glucuronoxylomannan mAb [Mukherjee, J., et al. Infect Immun 60:4534-4541 (1992)].

As is illustrated in Table I, 6 different phage clones were isolated with mAb CS40. In five of the clones a core motif of 4-5 residues in which a central tryptophan is flanked by hydrophilic amino acids (E/RWS/EXH/K) was observed.

TABLE 1

ManLAM peptide mimotopes

| Clone | Amino acid sequence | |
|---|---|---|
| A1 | WEADDKNQHGEG | (SEQ ID NO: 6) |
| B11 | ISLTEWSMWYRH | (SEQ ID NO: 1) |
| C1 | EEGPWSTHVGRT | (SEQ ID NO: 2) |
| C3 | WGNEGGDHLQPV | (SEQ ID NO: 3) |
| F7 | SLKIRWELKMYQE | (SEQ ID NO: 4) |
| G3 | AVERWSKHTWSE | (SEQ ID NO: 5) |

*The postulated motif amino acids are indicated in gray box and bold letters

Binding Properties of the Phage Clones and Synthetic Peptides (B11 and A1)

Efficiency of binding was evaluated by the magnitude of OD decrease when serial dilutions of phage clones were incubated with the CS40 mAb. The phage clones with the higher affinity to mAb showed maximum inhibition of the binding of the mAb to ManLAM with the lowest number of phage particles. When testing the clones that bound the CS40 mAb, two clones, B11 and C1, competed most efficiently with ManLAM (FIG. 1A); $1 \times 10^{11}$ phage particles per well reduced the OD by 100%. While with clone G3, a similar reduction in the OD was measured, however, it was obtained with $1 \times 10^{14}$ phage particles per well.

The synthetic B11 peptide bound the CS40 mAb, as tested by direct ELISA, and competed with ManLAM in binding to the mAb, as tested in competitive ELISA (100% decrease in OD with 50 µg/ml of peptide (FIG. 1B). The competitive binding properties were compared to those of a peptide corresponding to the sequence of clone A1. A1 peptide did not compete in the binding of the antibodies vs. ManLAM, thus indicating that the internal aromatic residue and adjacent hydrophilic residues present in the other mimotopes, such as in B11 peptide, are important for the binding to the CS40 mAb.

Antigenic Properties of B11 Phage Clone and Synthetic Peptide

B11 phage clone was tested for the ability to induce ManLAM-binding Abs in sera of immunized mice. Mice (n=5) injected twice with the B11 phage clone developed IgG antibodies specific to ManLAM, compared to naive mice and mice immunized with a control phage, as demonstrated by a serological ELISA test (FIG. 2A).

The antigenic properties of the B11 synthetic peptide was tested for the ability to induce IgM and IgG ManLAM binding Abs. This was performed by immunizing groups of five mice (n=5 per group) with the B11 synthetic peptide conjugated to KLH via an extra cystiene residue at the N-terminus. Significant levels of IgM Abs, which bound specifically to ManLAM, were detected in mice vaccinated s.c. with 50 µg peptide conjugated to KLH emulsified in the MPL-TDM adjuvant system, two weeks after the first immunization (p<0.05 vs. the control groups) (FIG. 2B). In the group vaccinated s.c. with 50 µg peptide conjugated to KLH in MPL-TDM, no significant levels of IgG were found after the first immunization. Significant levels (p<0.05 vs. the control groups) of specific ManLAM-binding IgG Abs were detected three weeks after the second s.c. immunization (FIG. 2C). The IgGs were mostly of the subtype IgG1 (FIG. 2D). These results were reproduced in three separate experiments. No significant ManLAM-binding antibody levels were detected in any of the other immunized groups (data not shown).

Covalently conjugating the polysaccharide antigen to a carrier protein was used as it improves the immune response by permitting the host to utilize a T-cell dependent immune response [Jacobson, R. M., and Poland, G. A. Minerva Pediatr 54:295-303 (2002)].

IgG Antibodies That Bind to the B11 Synthetic Peptide in Mtb-infected Mice

Figure 3:
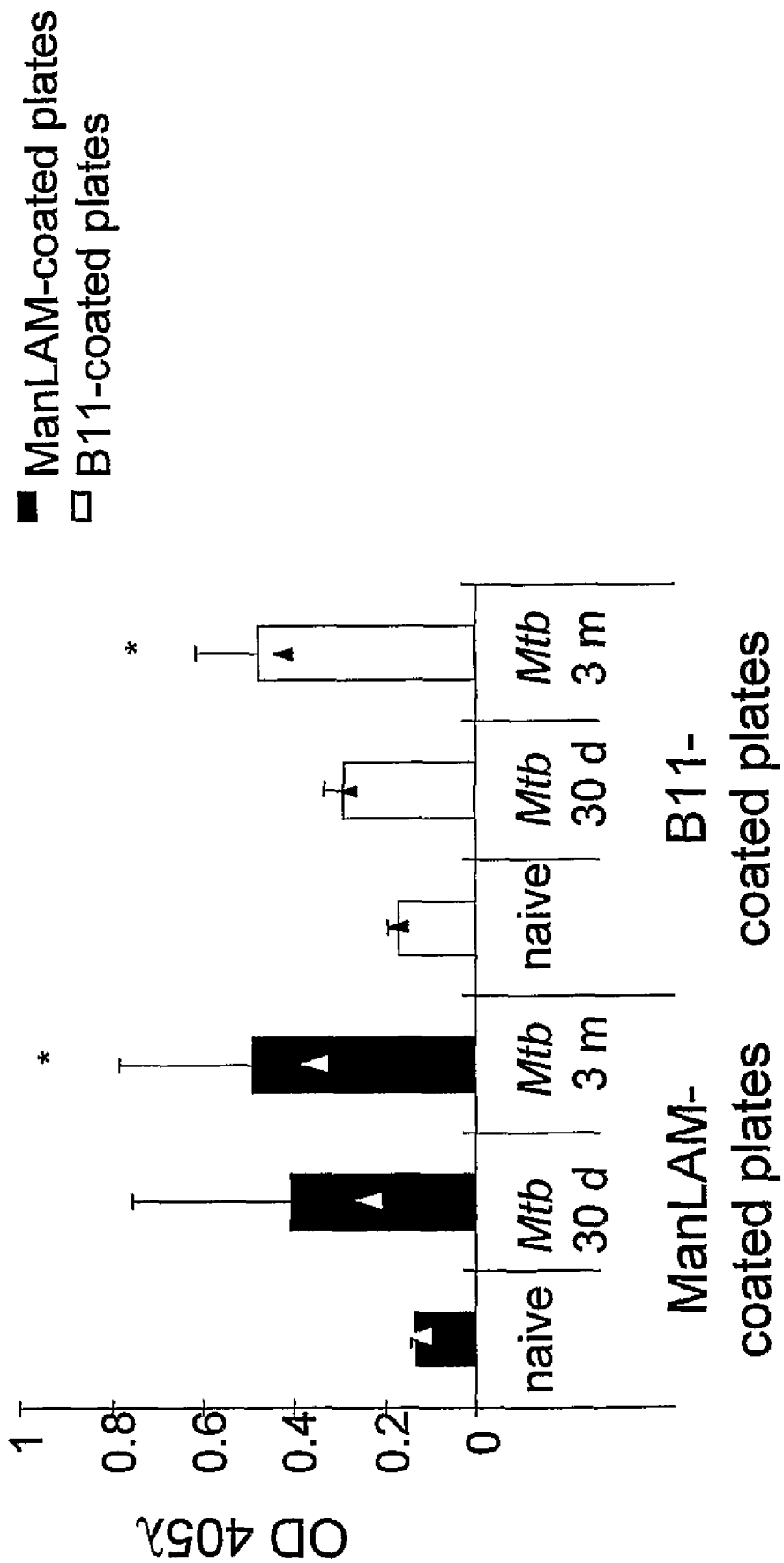
FIG. 3 Is a bar graph showing binding of antibodies from sera of 30 days and 3 month Mtb infected mice to ManLAM or B11 mimotope coated plates, as compared to naive mice.

To further investigate if the B11 peptide is a true mimotope of the ManLAM, mice experimentally infected with Mtb that have never been exposed to the peptide were tested for development of antibodies that recognize the B11 peptide, similar to the Abs developed against ManLAM. To this end, thirty days (n=6) and three months (n=4) after an experimental Mtb infection, sera of BALB/c mice were tested for the presence of IgG that recognized ManLAM and B11 peptide, and were compared to naive mice (n=6). In the Mtb-infected mice IgG Abs which binds both ManLAM and B11 peptide were detected, at levels significantly higher than those of the naive mice (p<0.01). The antibody levels binding ManLAM as well as to B11 peptide were similar (FIG. 3). The same results were obtained when the ELISA assay was performed with or without the extra cysteine at the amino teriminus of the synthetic peptide (data not shown). This gave additional evidence that the peptide with the cysteine (SEQ ID NO: 10, CISLTEWSMWYRH) maintained binding properties to ManLAM-binding antibodies as the original peptide selected (SEQ ID NO: 1, ISLTEWSMWYRH).

IgG Peptide-binding Antibodies in Human Tuberculosis Patients

Figure 4:
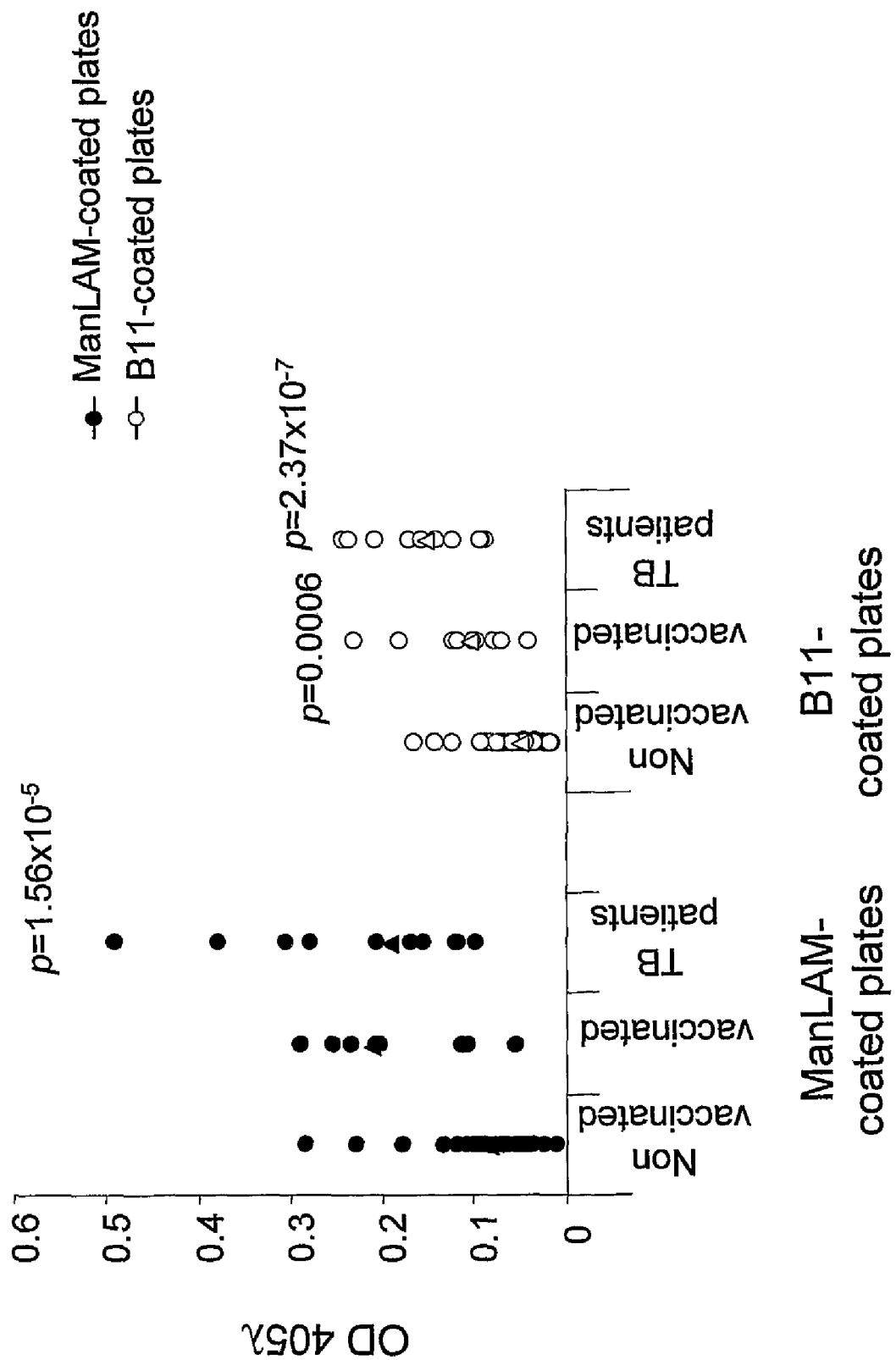
FIG. 4 is a graph showing antibodies in TB human patients sera binding to ManLAM and the B11 mimotope, compared to non-vaccinated healthy individuals and BCG-vaccinated healthy, individuals. Median represented by triangle. The OD presented is the average $OD_{405}$ value of each triplicate sample.

High levels of anti-ManLAM antibodies were measured in tuberculosis (TB) patients [Hamasur, B., et al. J Microbiol Methods 45:41-52 (2001)]. The presence of serum antibodies in sera of TB patients that bind the B11 peptide was tested. Significantly higher titers of ManLAM and B11 peptide-binding antibodies in sera of TB patients (n=16) than in sera of healthy individuals (n=36) were found (FIG. 4). Like the antibody levels measured in mice, the human anti-ManLAM and B11 peptide-binding antibody levels were similar, but the variability of the serum titers (SD=0.129 for ManLAM vs. SD=0.058 for the peptide) was smaller when using the B11 peptide as an antigen in the ELISA test (FIG. 4). This might indicate that the peptide can be a more reliable reagent than ManLAM for serological diagnosis. Using ELISA, sera from Bacillus Calmette Guerin (BCG)-vaccinated individuals (n=10) was tested, as it is sometimes difficult to distinguish BCG-vaccinated individuals from TB patients [Ciesielski, S. D., J Fam Pract 40:76-80 (1995)]. The anti-peptide antibody titers measured in BCG-vaccinated individuals were significantly lower than in TB patients (p<0.001) (FIG. 4). Standard deviation (SD) values were smaller in all groups when using the B11 peptide as an antigen compared to the SD values in binding ManLAM as an antigen. SD values of B11 peptide coated plates: Non-vaccinated—SD=0.035, Vaccinated—SD=0.058 TB patients—SD=0.05874. SD values of ManLAM-coated plates: Non-vaccinated—SD=0.057, Vaccinated—SD=0.084, TB-patients—SD=0.129.

Thus, use of the B11 peptide and the like, as defined herein, as the antigen in an ELISA test provides a new and accurate tool to discriminate between TB patients, healthy BCG-vaccinated and non-vaccinated individuals.

B11 Peptide Binds the Murine Macrophage Cell Line RAW 264.7

Figure 5A:
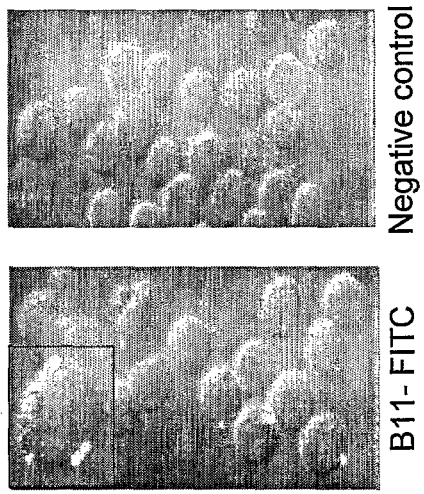
FIGS. 5A-5C are images showing the binding of B11 FITC-labeled peptide to the macrophage RAW 264.7 cell line as is illustrated by confocal micrograph (FIG. 5A) and FACS analysis (FIG. 5B), quantifying the fluorescence levels corresponding to the binding of the B11 FITC-labeled peptide, and the reduction of binding when 0.125 M D-mannose was added (FIG. 5C).
Figure 5B:
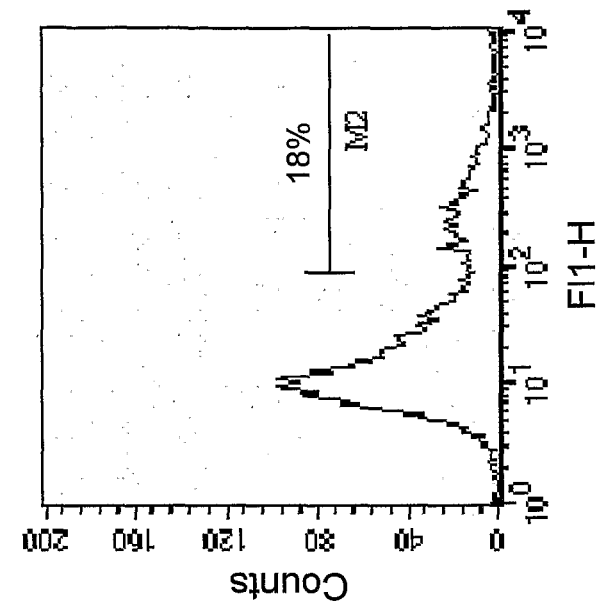
Figure 5C:
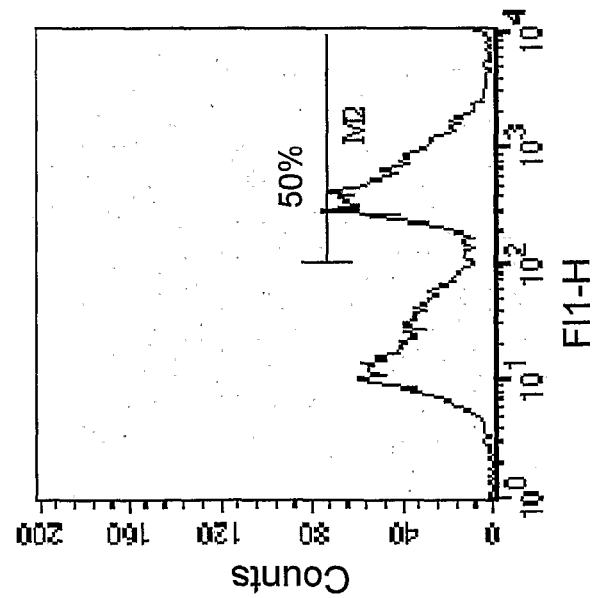

ManLAM binds macrophages via mannose-binding receptors [Maeda, N., et al. J Biol Chem 278:5513-5516 (2003)]; therefore, the binding of the peptide mimotope of ManLAM to macrophages was examined. Indeed, the FITC-conjugated B11 peptide bound the macrophage cell line RAW 264.7, as seen by confocal microscopy (FIG. 5A) and FACS analysis (FIG. 5B). The binding of the B11 peptide to the macrophages was inhibited by D-mannose, as detected by FACS analysis (FIG. 5C), indicating that the peptide binds a macrophage mannose receptor.

The invention claimed is:

1. A molecule comprising:

an isolated peptide comprising an amino acid sequence comprising SEQ ID NO: 1.

2. The molecule of claim 1, wherein the isolated peptide is capable of binding to mannosylated lipoarabinomannan (ManLAM) binding antibodies.

3. The molecule of claim 1, wherein the ManLAM-binding antibodies are monoclonal antibodies (mAbs) or anti ManLaM antibodies.

4. The molecule of claim 3, wherein the mAbs are CS40 antibodies.

5. The molecule of claim 1, which does not bind to antibodies directed against lipoglycans selected from the group consisting of non-mannolsylated and low mannosylated lipoglycans.

6. The molecule of claim 5, which does not bind to CS35 anti-lipoarabinomannan (LAM) mAb, 735 anti-ploy α(2→8) N-acetyl neuraminic acid mAb, and 2H1 anti-glucuronoxylomannan mAb.

7. A kit comprising a molecule comprising an isolated peptide comprising an amino acid sequence comprising SEQ ID NO: 1.

8. An immunizing composition comprising an immunologically acceptable adjuvant and an isolated peptide molecule comprising the amino acid sequence of SEQ ID NO: 1, wherein the peptide molecule is conjugated to a carrier protein.

9. The composition of claim 8, wherein the isolated peptide molecule is capable of binding to anti-ManLAM antibodies.

10. The composition of claim 8, wherein the isolated peptide molecule does not bind to antibodies directed against lipoglycans selected from non-mannosylated and low mannosylated lipoglycans.

11. The composition of claim 10, wherein the isolated peptide molecule does not bind to CS35 anti-lipoarabinomannan (LAM) mAb, 735 anti-ploy α(2→8)N-acetyl neuraminic acid mAb, and 2H1 anti-glucuronoxylomannan mAb.

12. A method of eliciting Man-LAM-binding antibodies in a mammalian subject, the method comprising administering to said subject an immunizing amount of the composition of claim 8.

13. The method of claim 12, wherein the isolated peptide molecule does not bind to antibodies directed against lipoglycans selected from non-mannolsylated and low mannosylated lipoglycans.

14. The method of claim 13, wherein the isolated peptide molecule does not bind to CS35 anti-lipoarabinomannan (LAM) mAb, 735 anti-ploy α(2→8)N-acetyl neuraminic acid mAb, and 2H1 anti-glucuronoxylomannan mAb.

* * * * *

UNITED STATES PATENT AND TRADEMARK OFFICE
CERTIFICATE OF CORRECTION

PATENT NO. : 7,892,557 B2  
APPLICATION NO. : 10/589866  
DATED : February 22, 2011  
INVENTOR(S) : Herve Bercovier, Ayelet Barenholz and Jonathan Gershoni Page 1 of 1

It is certified that error appears in the above-identified patent and that said Letters Patent is hereby corrected as shown below:

On the Title page please delete:

Item "(73) Assignee: Yissum Research Development Company of The Hebrew University of Jerusalem, Jerusalem (IL)"

and replace with:

Item -- (73) Assignee: Yissum Research Development Company of The Hebrew University of Jerusalem, Jerusalem (IL); Ramot at Tel-Aviv University Ltd., Tel Aviv, (IL) --

Signed and Sealed this  
Twenty-first Day of June, 2011

David J. Kappos  
*Director of the United States Patent and Trademark Office*

SEQUENCE LISTING

<160> NUMBER OF SEQ ID NOS: 10

<210> SEQ ID NO 1
<211> LENGTH: 12
<212> TYPE: PRT
<213> ORGANISM: Artificial sequence
<220> FEATURE:
<223> OTHER INFORMATION: random phage display library

<400> SEQUENCE: 1

Ile Ser Leu Thr Glu Trp Ser Met Trp Tyr Arg His
1               5                   10

<210> SEQ ID NO 2
<211> LENGTH: 12
<212> TYPE: PRT
<213> ORGANISM: Artificial sequence
<220> FEATURE:
<223> OTHER INFORMATION: random phage display library

<400> SEQUENCE: 2

Glu Glu Gly Pro Trp Ser Thr His Val Gly Arg Thr
1               5                   10

<210> SEQ ID NO 3
<211> LENGTH: 12
<212> TYPE: PRT
<213> ORGANISM: Artificial sequence
<220> FEATURE:
<223> OTHER INFORMATION: random phage display library

<400> SEQUENCE: 3

Trp Gly Asn Glu Gly Gly Asp His Leu Gln Pro Val
1               5                   10

<210> SEQ ID NO 4
<211> LENGTH: 13
<212> TYPE: PRT
<213> ORGANISM: Artificial sequence
<220> FEATURE:
<223> OTHER INFORMATION: random phage display library

<400> SEQUENCE: 4

Ser Leu Lys Ile Arg Trp Glu Leu Lys Met Tyr Gln Glu
1               5                   10

<210> SEQ ID NO 5
<211> LENGTH: 12
<212> TYPE: PRT
<213> ORGANISM: Artificial sequence
<220> FEATURE:
<223> OTHER INFORMATION: random phage display library

<400> SEQUENCE: 5

Ala Val Glu Arg Trp Glu Lys His Thr Trp Ser Glu
1               5                   10

<210> SEQ ID NO 6
<211> LENGTH: 12
<212> TYPE: PRT
<213> ORGANISM: Artificial sequence
<220> FEATURE:
<223> OTHER INFORMATION: random phage display library

<400> SEQUENCE: 6

-continued

Trp Glu Ala Asp Asp Lys Asn Gln His Gly Glu Gly
1 5 10

<210> SEQ ID NO 7
<211> LENGTH: 5
<212> TYPE: PRT
<213> ORGANISM: Artificial sequence
<220> FEATURE:
<223> OTHER INFORMATION: random phage display library

<400> SEQUENCE: 7

Trp Ser Met Trp Tyr
1 5

<210> SEQ ID NO 8
<211> LENGTH: 6
<212> TYPE: PRT
<213> ORGANISM: Artificial sequence
<220> FEATURE:
<223> OTHER INFORMATION: random phage display library

<400> SEQUENCE: 8

Trp Glu Leu Lys Met Tyr
1 5

<210> SEQ ID NO 9
<211> LENGTH: 6
<212> TYPE: PRT
<213> ORGANISM: Artificial sequence
<220> FEATURE:
<223> OTHER INFORMATION: random phage display library

<400> SEQUENCE: 9

Trp Glu Lys His Thr Trp
1 5

<210> SEQ ID NO 10
<211> LENGTH: 13
<212> TYPE: PRT
<213> ORGANISM: Artificial sequence
<220> FEATURE:
<223> OTHER INFORMATION: random phage display library

<400> SEQUENCE: 10

Cys Ile Ser Leu Thr Glu Trp Ser Met Trp Tyr Arg His
1 5 10